United States Patent

Champseix et al.

[11] 4,294,841
[45] Oct. 13, 1981

[54] DERIVATIVES OF 1-PHENYL 3-(4-PIPERIDYL) 1-PROPANONE USABLE AS DRUGS

[75] Inventors: Alain A. Champseix, Forges les Bains; Gerard R. Le Fur, Plessis Robinson, both of France

[73] Assignee: Pharmindustrie, Gennevilliers, France

[21] Appl. No.: 97,772

[22] Filed: Nov. 27, 1979

[30] Foreign Application Priority Data

Dec. 5, 1978 [FR] France ................... 78 34185

[51] Int. Cl.$^3$ .................. A61K 31/445; C07D 211/32
[52] U.S. Cl. ...................... 424/267; 424/263; 546/192; 546/232; 546/235; 546/236; 546/237; 546/240; 546/329; 546/334; 546/337; 546/338; 546/340; 546/344
[58] Field of Search ............ 546/237, 235, 232, 236, 546/240, 192, 329, 334, 337, 338, 340, 344; 424/267, 263

[56] References Cited

U.S. PATENT DOCUMENTS 2,833,776 5/1958 Ruddy ........................ 546/237
3,637,712 1/1972 Partyka et al. .............. 546/240
4,181,803 1/1980 Morita et al. ............... 546/237

OTHER PUBLICATIONS

Morrison and Boyd "Organic Chemistry" 3rd Edition, (1973) pp. 625–627, 671–272.

Primary Examiner—Robert T. Bond
Attorney, Agent, or Firm—Beveridge, DeGrandi, Kline & Lunsford

[57] ABSTRACT

A drug useful as antiarhythmic, antidepressant and anxiolytic containing as an active agent a compound of the formula

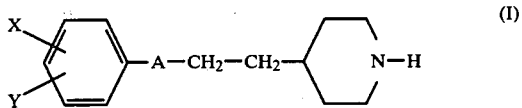

(I)

wherein X and Y are the same or different and represent hydrogen or halogen atoms, or 1–4C alkyl groups, 1–4C alkoxy groups, 1–4C alkylthio groups, CF$_3$, OH, NH$_2$, 1–4C monoalkylamino or amino groups substituted by a 1–4C alkylsulfonyl group, a 1–5C alkylcarbonyl group or an aroyl group and A is a CO, CHOH or CH$_2$ group, or a salt of said compound with a pharmaceutically acceptable acid, is disclosed together with methods for the preparation thereof and its use in human therapy.

8 Claims, No Drawings

DERIVATIVES OF 1-PHENYL 3-(4-PIPERIDYL) 1-PROPANONE USABLE AS DRUGS

The present invention relates to new drugs, useful notably as antiarythmics and as psychotropics, in particular for the treatments of states of depression and anxiety, containing as active agent a derivative of 1-phenyl 3-(4-piperidyl) 1-propanone corresponding to formula (I) below or a salt of such compound with a pharmaceutically acceptable acid.

The derivatives of 1-phenyl 3-(4-piperidyl) 1-propanone incorporated as active agent in the drugs in accordance with the invention may be represented by the formula:

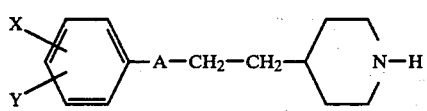
(I)

wherein X and Y are the same or different and represent hydrogen or halogen (chlorine, fluorine, bromine or iodine) atoms, alkyl groups containing 1 to 4 carbon atoms, alkoxy groups containing 1 to 4 carbon atoms, alkylthio groups containing 1 to 4 carbon atoms, trifluoromethyl, hydroxy, amino, monoalkylamino groups containing 1 to 4 carbon atoms or amino groups substituted by an alkylsulfonyl group containing 1 to 4 carbon atoms, by an alkylcarbonyl group containing 1 to 5 carbon atoms, in particular acetyl, or by an aroyl group, in particular benzoyl, and A represents a

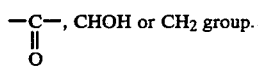

The compounds of formula (I) wherein A is $CH_2$, Y is a hydrogen atom and X is a hydrogen atom or a p-methoxy, m-methoxy, o-methoxy, p-methyl, p-isopropyl or p-tert. butyl group are already known. They have been described as synthesis intermediates (see DOS No. 2,456,947; Belgian Pat. No. 818,260; Prasad et al. J. Chem. Soc. (C) 1969. 2134–2136; E. O. Magarian et al. J. Pharm. Sci. 62, 325, 1973), but none of these compounds up to now has been recommended as a drug.

The compounds of formula (I), other than those recited in the preceding paragraph, are new and as such form part of the present invention.

The products of general formula (I) wherein A represents the $CH_2$ group may be prepared by reduction of the corresponding products of formula (I) wherein A represents the CO group or their N-benzoylated derivatives (the removal of the benzoyl grouping being effected under the conditions of the reduction). For this reduction, methods known in themselves are used, which allow the conversion of a CO group to a $CH_2$ group, for example those described by R. B. Wagner and H. D. Zook, Synthetic Organic Chemistry p. 5 (J. Wiley and Sons - 1953).

As a reducing agent it is advantageous to use hydrazine hydrate in the presence of an alkali metal hydroxide, such as sodium hydroxide, in a solvent such as an alcohol. The operation generally takes place at the boiling point of the solvent.

The products of general formula (I) wherein A represents the $CH_2$ grouping may also be prepared by catalytic hydrogenation of compounds containing the pyridine nucleus of the formula:

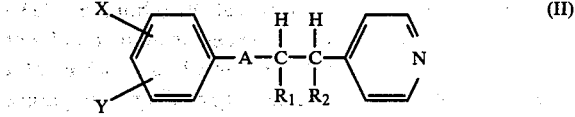
(II)

or their salts.

In formula (II), A, X and Y have the same definitions as in formula (I), $R_1$ represents a hydrogen atom, $R_2$ represents a hydrogen atom or an OH group, $R_1$ and $R_2$ together, moreover, may form a single bond.

The products of formula (II) which are preferred because they are the most accessible are the following:

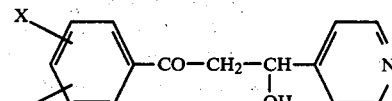
(II$_A$)

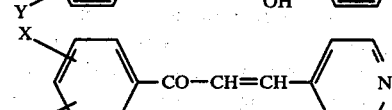
(II$_B$)

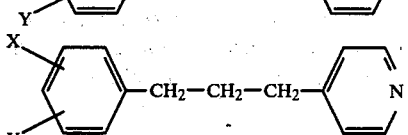
(II$_C$)

This catalytic hydrogenation is effected in an inert solvent and in the presence of a catalyst, at a temperature ranging from 20° C. to 80° C. and under a hydrogen pressure of 1 to 50 bars. As a solvent it is possible, for example, to use alcohols, such as methanol or ethanol, or acids such as acetic acid. Catalysts which may be used include nickel, palladium, rhodium, ruthenium or platinum.

The compounds of general formula (I) wherein A represents a $CH_2$ grouping and at least one of the substituents X and Y is an $NH_2$ group may also be prepared by catalytic hydrogenation, under conditions identical to those employed for the hydrogenation of the compounds of formula (II), of compounds of the formula:

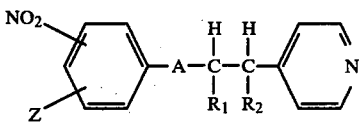
(III)

wherein A is

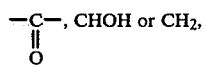

$R_1$ and $R_2$ have the definitions set forth above and Z has the same definition as do X and Y in formula (I).

The compounds of formula (I) wherein A represents the CHOH group may be prepared by reduction of the corresponding compounds of formula (I) wherein A represents the CO group. For this purpose procedures, known in themselves, for the conversion of a ketone to an alcohol may be used (see R. B. Wagner and H. D. Zook, Synthetic Organic Chemistry, p. 149-J. Wiley and Sons, 1953). It is advantageous to use as a reducing agent a metal hydride such as sodium, potassium or lithium borohydride, lithium aluminum hydride, bis-(2-methoxy ethoxy) aluminum hydride or diborane. These hydrides are generally used in excess in an inert solvent such as ether, tetrahydrofurane or a hydrocarbon, at a temperature between 10° C. and the boiling temperature of the solvent used.

The products of general formula (I) wherein A represents the CO group may be prepared by incomplete catalytic hydrogenation of the products of formula (II$_B$) or of their salts. It is appropriate to stop the hydrogenation when the quantity of hydrogen theoretically required for the hydrogenation of the —CH═CH— group and of the pyridine ring has been absorbed. The operation is generally carried out near to ambient temperature, under a hydrogen pressure close to atmospheric pressure, in an inert solvent such as an alcohol (for example, methanol or ethanol) or an acid (for example, acetic acid). Catalysts which may be used include palladium, rhodium, ruthenium and platinum.

The compounds of formula (I) wherein A represents the CO group may also be prepared by a Friedel-Crafts acylation reaction, allowing a benzene derivative of formula (IV) to react with a piperidine derivative of formula (V) and hydrolyzing the compound of formula (VI) so formed, according to the following reaction scheme:

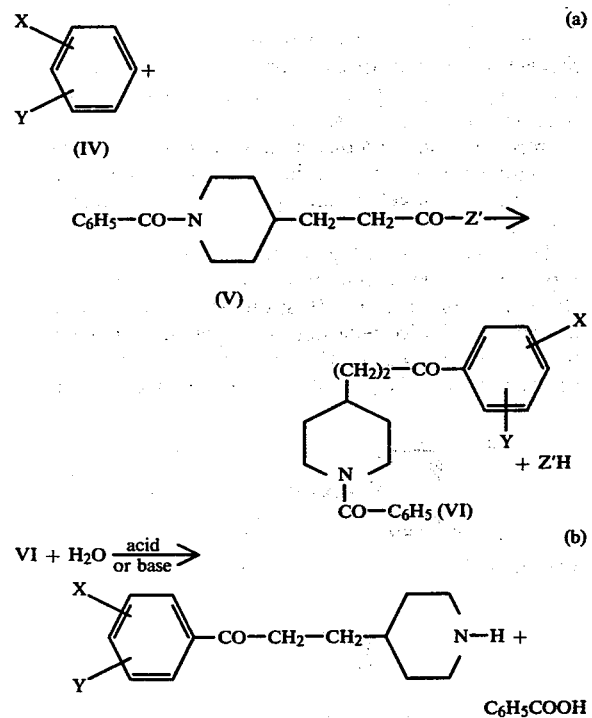

In formula (V) Z' designates an OH group or a halogen atom.

To realize reation (a), the operation is carried out in the presence of catalysts known under the name of Friedel-Crafts catalysts (metal halides, metal oxides, iodine, mineral acids, etc.) under conditions such as those described in "Friedel-Crafts and Related Reactions" Olah, Vol. 3 (Interscience 1964). When Z' represents a chlorine atom it is advantageous to use aluminum chloride as the catalyst, in the presence or absence of a solvent, the solvents used being preferably carbon disulfide or 1,2-dichloroethane. When Z' is an OH group it is possible, for example, to operate in the presence of phosphoric acid at a temperature of approximately 100° C.

The hydrolysis reaction (b) is carried out according to methods known in themselves (see, e.g., "Hydrolysis of N-substituted Amides" in "Synthetic Organic Chemistry" p. 678, R. B. Wagner and and H. D. Zook, J. Wiley and Sons, 1953). It may be effected, for example, by means of an aqueous solution, heated to reflux, of a mineral acid such as hydrochloric acid or sulfuric acid or of an inorganic base such as sodium hydroxide or potassium hydroxide.

According to the nature of the substituents X and Y, the yield of reaction (a) thus varies, as does the position on the benzene ring where the acylation perponderantly takes place (see J. March "Advanced Organic Chemistry Reactions, Mechanisms and Structure" McGraw Hill, 1968, pp. 382 to 391). The method making use of the Friedel-Crafts acylation reaction is advantageous in the case wherein X is a hydrogen or halogen atom or an alkyl or alkoxy group and y is a hydrogen atom or a group identical with X, not situated in para-position with respect to X. In that case the reaction takes place with a good yield and the products obtained carry the acyl chain in para-position with respect to the X grouping.

The reaction mixtures obtained by the methods described above are treated according to traditional methods, physical (evaporation, solvent-extraction, distillation, crystallization, chromatography, etc.) or chemical (salt formation and regeration of base, etc.) in order to separate the product of formula (I) in the pure state.

The compounds of formula (I) in the form of free bases may, if desired, be converted to addition salts with an inorganic or organic acid through the action of such an acid in a suitable solvent.

Certain compounds corresponding to formulae (II$_A$), (II$_B$) and (II$_C$) are already known. The compound of formula (II$_A$) wherein Y is H and X is OH in position 2 has been described by A. Corvaisier (Bull. Soc. Chim. Fr. 1962, 528–534). The compounds of formula (II$_B$) with X=Y=H and with X=OH in position 2 and Y=H, OCH$_3$ in position 4, Cl or Br in position 4 or 5 have been described by A. Corvaisier (loc. cit.), C. S. Marvel et al. (J. Org. Chem. 1785 (1955)), A. C. Annigeri et al. (Monatsch. Chem. 96, 625 (1965)) and P. DeVitt et al. (J. Org. Chem. 26, 4941, (1961)). The compounds of formula (II$_C$) with Y=H and X=H, OCH$_3$ in position 2, 3 or 4, CH$_3$ in position 4, isopropyl in position 4, tert.-butyl in position 4 have been described by K. B. Prasad et al. (loc. cit.) and in DOS No. 2,456,947.

The compounds of formulae (II$_A$) and (II$_B$) may be prepared, according to a known general method (see Houben-Weyl, Methoden der Organischen Chemie 7 (2b) 1483), by condensing pyridine 4-carbaldehyde with an acetophenone of formula (VII) according to the reaction scheme:

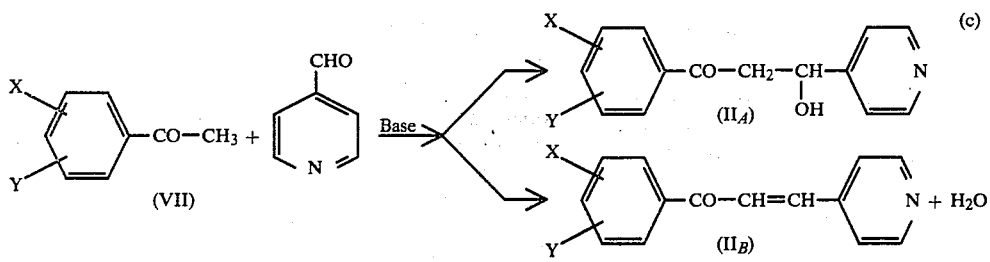

The condensation reaction (c) may be realized in a pure alcohol, such as methanol or ethanol, in the presence of a base such as tetramethylammonium hydroxide or a basic resin (for example, IRA-400), at ambient temperature. It is also possible to operate in the presence of sodium hydroxide in a hydroalcoholic medium. According to the conditions and according to the nature of the substituents X and Y, either the compound ($II_B$) or the compound ($II_A$) or a mixture of the two products is obtained, which may then be separated by crystallization or chromatography.

The compounds of formula ($II_C$) may be obtained in a general manner by non-catalytic reduction of the pyridine derivatives of the formula:

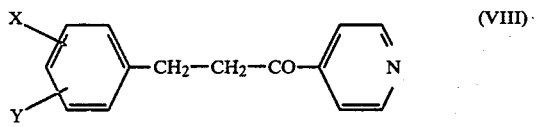

which in turn are obtained by condensation of 4-cyano pyridine with the appropriate organo-magnesium derivative according to the method described by K. P. Prasad et al. J. Chem. Soc. (C) 1969, 2134.

As a reducing agent hydrazine hydrate is used advantageously in the presence of an alkali metal hydroxide such as sodium hydroxide in a solvent such as alcohol. The operation is generally carried out at the boiling temperature of the solvent.

The compounds of formula (III), which are new and as such form part of the invention, may be prepared by nitration of compounds of the formula:

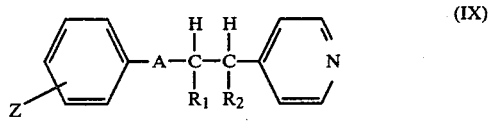

wherein A, $R_1$, $R_2$ and Z have the same definitions as in formula (III).

Certain compounds corresponding to formula (VI), in particular those described in the following Examples 1 to 5, are new.

The following examples illustrate the invention without limiting it. Examples 1 to 5 relate to the preparation of compounds of formula (VI), the Examples 11 to 15 to that of compounds of formula (II), and Examples 6 to 10 and 16 to 22 so that of compounds of formula (I). The nuclear magnetic resonance spectra appearing in the examples are those of the proton.

EXAMPLE 1

3-(1-Benzoyl 4-piperidyl) 1-(4-methoxyphenyl) 1-propanone

A solution of 9.9 g of anisol in 157 ml of carbon disulfide is stirred vigorously with 17 g of 3-(benzoyl 4-piperidyl) propionyl chloride (prepared by the action of 8.8 ml of thionyl chloride on 15.7 g of 3-(1-benzoyl 4-piperidyl) propionic acid in chloroform). Then 20.2 g of finely divided aluminum chloride are added in portions. The temperature progressively rises to 35° C. The mixture is heated to 50° C. over a period of 20 minutes and is then poured into crushed ice and extracted twice with 200 ml of chloroform. The collected organic phases are washed with water, dried over magnesium sulfate, then concentrated by elimination of chloroform. The residual oil obtained is recrystallized in 200 ml of an ether/petroleum ether mixture and the crystals obtained are dried at 65° C. under vacuum.

In this manner 16.7 g of 3-(benzoyl 4-piperidyl) 1-(4-methoxy phenyl) 1-propanone are obtained.

NMR (Nuclear Magnetic Resonance) spectrum of the product obtained (solvent: Deuterochloroform; reference: Tetramethylsilane):

The chemical shifts δ are as follows:

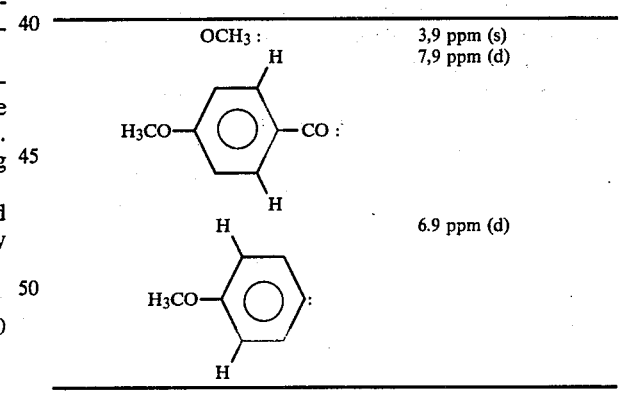

The 3-(1-benzoyl 4-piperidyl) propionic acid used as the starting product has been described by Koelsch (J. Am. Chem. Soc. 1943, 65, 2460).

EXAMPLE 2

3-(1-Benzoyl 4-piperidyl) 1-(4-fluorophenyl) 1-propanone

The procedure is as in Example 1, starting from 8.8 g of fluorobenzene instead of the 9.9 g of anisol and from 20 g instead of from 15.7 g of 3-(1-benzoyl 4-piperidyl) propionic acid. 25.5 g of crude 3-(1-benzoyl 4-piperidyl) 1-(4-fluorophenyl) 1-propanone in the form of an oil are obtained.

EXAMPLE 3

1-(3,4-Dichlorophenyl) 3-(1-benzoyl 4-piperidyl) 1-propanone

In Example 1 the 9.9 g of anisole and the 15.7 g of 3-(1-benzoyl 4-piperidyl) propionic acid are substituted by 185 ml of 1,2 dichlorobenzene and 35 g of 3-(1-benzoyl 4-piperidyl) propionic acid respectively. The reaction is effected at 100° C. and without solvent. 51.1 g of crude 1-(3,4-dichlorophenyl) 3-(1-benzoyl 4-piperidyl) 1-propanone in the form of an oil which crystallizes slowly are obtained.

EXAMPLE 4

1-(4-Chlorophenyl) 3-(1-benzoyl 4-piperidyl) 1-propanone

The procedure is as in Example 1, starting from 18 g of chlorobenzene instead of 9.9 g of anisol, 350 ml of carbon disulfide instead of 157 ml and 35 g instead of 15.7 g of 3-(1-benzoyl 4-piperidyl) propionic acid. 40.1 g of crude 1-(4-chlorophenyl) 3-(1-benzoyl 4-piperidyl) 1-propanone are obtained in the form of an oil which crystallizes.

EXAMPLE 5

1-(4-Methylphenyl) 3-(1-benzoyl 4-piperidyl) 1-propanone

The procedure is as in Example 4, substituting the 18 g of chlorobenzene by 30 g of toluene. 34 g of crude 1-(4-methylphenyl) 3-(1-benzoyl 4-piperidyl) 1-propanone are obtained in the form of an oil.

EXAMPLE 6

4-[3-(4-Methoxyphenyl) 1-propyl]piperidine

Over a period of 20 minutes a solution containing 16.7 g of 3-(1-benzoyl 4-piperidyl) 1-(4-methoxyphenyl) 1-propanone, 45 ml of diethylene glycol and 8.4 g of 85% hydrazine hydrate is heated to 140° C. The yellow solution obtained is cooled to 100° C., then 16 g of potassium hydroxide in pellets are added in portions. The temperature is maintained at 160° C. for 4 hours, then at 190° C. for 2 hours. The mixture is cooled and 450 ml of water are added. The mixture is extracted twice with 150 ml of ethyl acetate, then the organic phase is dried with magnesium sulfate. After filtration and concentration by elimination of the ethyl acetate, an oil is obtained which, acidified with a solution of hydrochloric acid in acetone, furnished 10.2 g of the hydrochloride of 4-[3-(4-methoxyphenyl) 1-propyl]piperidine which melts at 145° C.

Analysis for $C_{15}H_{23}NO$, HCl: Calc. % C 66.8; % H 8.91; % N 5.19. Found % C 66.60; % H 8.85; % N 5.01.

EXAMPLE 7

4-[3-(4-Fluorophenyl)1-propyl]piperidine

The procedure is as in Example 6 starting from 24.2 g of 3-(1-benzoyl 4-piperidyl) 1-(4-fluorophenyl) 1-propanone. 8.7 g of 4-[3-(4-fluorophenyl)1-propyl]piperidine are obtained in the form of the hydrochloride melting at 142° C.

Analysis for $C_{14}H_{20}NF$, HCl: Calc. % C 65.2; % H 8.16; % N 5.44. Found % C 65.2; % H 8.22; % N 5.41.

EXAMPLE 8

4-[3-(4-Chlorophenyl)1-propyl]piperidine

The procedure is as in Example 6 starting from 40.1 g of 3-(1-benzoyl 4-piperidyl) 1-(4-chlorophenyl) 1-propanone. 23.5 g of a brown oil are obtained, which after acidification with HCl and recrystallization furnishes 19.6 g of 4-[3-(4-chlorophenyl)1-propyl]piperidine in the form of the hydrochloride which melts at 142° C.

NMR spectrum of the product obtained (solvent: $CDCL_3$; reference: Tetramethylsilane):
Protons of the aromatic nucleus (in abridged form, aromatic): $\delta = 6.8$ to $7.4$ ppm (m)
$CH_2$—N and $CH_2$—Ar: $\delta = 2.4$ to $3.3$ pp, (m)

EXAMPLE 9

4-[3-(3,4-Dichlorophenyl)1-phenyl]piperidine

The procedure is as in Example 6 starting from 51.1 g of 3-(1-benzoyl 4-piperidyl) 1-(3,4-dichlorophenyl) 1-propanone. 15.3 g of 4-[3-(3,4-dichlorophenyl)1-propyl]piperidine in the form of the hydrochloride melting at 150° C. are obtained.

NMR spectrum of the product obtained (solvent $CHCL_3$):
Aromatic: $\delta = 6.8$ to $7.4$ ppm (m)
$CH_2$—N and $CH_2$—Ar: $\delta = 2.4$ to $3.3$ ppm(m)

EXAMPLE 10

4-[3-(4-Methylphenyl)1-propyl]piperidine

The procedure is as in Example 6 starting from 34.2 g of 3-(1-benzoyl 4-piperidyl) 1-(4-methylphenyl) 1-propanone. 12 g of 4-[3-(4-methylphenyl)1-propyl]piperidine which melts at 171° C. are obtained.

NMR spectrum of the product obtained (solvent $CDCl_3$):
Aromatic: $\delta = 7$ ppm (s)
$CH_3$—Ar: $\delta = 2.3$ ppm (s)
$CH_2$—N and $CH_2$—Ar: $\delta = 2.3$ to $3.3$ ppm (m)

EXAMPLE 11

1-(2-Hydroxyphenyl) 3-(4-pyridyl) 3-hydroxyl 2-propanone

According to the method of Corvaisier (Bull. Soc. Chim. Fr. 1962, 528) 15 ml of an 11 N aqueous sodium hydroxide solution are added to a solution of 24 g of 2-hydroxyacetophenone and 21 g of pyridine-4-carbaldehyde in 130 ml of absolute ethanol maintained an ambient temperature. An abundant yellow precipitate forms at first which then gradually dissolves. After two hours at ambient temperature the mixture is adjusted to pH 1 by means of hydrochloric acid. The yellow precipitate obtained is filtered, washed with water and dried. 27 g of 1-(2-hydroxyphenyl) 3-(4-pyridyl) 3-hydroxy 1-propanone melting at 150° C. are obtained.

NMR spectrum of the product obtained (solvent: trifluoroacetic acid):
—$CH_2$ (CHOH): $\delta = 3.3$ ppm (d)
CHOH: $\delta = 5.5$ ppm (t)

EXAMPLE 12

1-(4-Aminophenyl) 3-(4-pyridyl) 2-propene-1-one

The procedure is as in Example 11, starting from 1.35 g of 4-aminoacetophenone (instead of 24 g of 2-hydroxyacetophenone) and 2.14 g of pyridine-4-carbaldehyde instead of 21 g and using a 2.5 N aqueous sodium hydroxide solution instead of an 11 N solution. 2.2 g of 1-(4-aminophenyl) 3-(4-pyridyl) 2-propene-1-one which melts at 207° C. are obtained.

NMR spectrum of the product obtained (solvent: trifluoroacetic acid):

  δ = 7.4 ppm (d)
                      7.7 ppm (d)

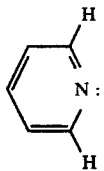  δ = 8.6 ppm (d)

EXAMPLE 13

1-(4-Fluorophenyl) 3-(4-pyridyl) 2-propene-1-one

The procedure is as in Example 11 starting from 2.9 g of 4-fluoroacetophenone and 3 g of pyridine-4-carbaldehyde, but using a solution of tetramethylammonium hydroxide in methanol instead of the aqueous solution of sodium hydroxide. 1-(4-fluorophenyl) 3-(4-pyridyl) 2-propene-1-one which melts at 157° C. is obtained.

NMR spectrum of the product obtained (solvent CDCl$_3$):

  δ = 7.6 ppm (s)

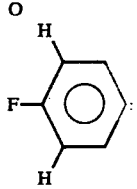  δ = 7.2 ppm (t)

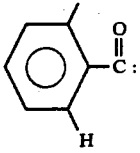  δ = 8 ppm (d d)

EXAMPLE 14

1-(2-Aminophenyl) 3-(4-pyridyl) 2-propene-1-one

The procedure is as in Example 13 starting from 4 g of 2-aminoacetophenone and 6.42 g of pyridine-4-carbaldehyde in 14 ml of methanol. 5.2 g of a 50/50 mixture of 1-(2-aminophenyl) 3-(4-pyridyl) 3-hydroxy 1-propanone and of 1-(2-aminophenyl) 3-(4-pyridyl) 2-propene-1-one are obtained. The constituents of this mixture are separated by chromatography on a silica column (eluant: mixture of 80 parts by volume of ethyl acetate and 20 parts by volume of cyclohexane). 2.3 g of 1-(2-aminophenyl) 3-(4-pyridyl) 2-propene-1-one, melting at 168° C. are obtained.

NMR spectrum of the product obtained (solvent CDCl$_3$):

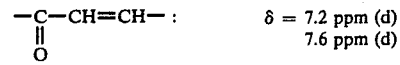  δ = 7.2 ppm (d)
                      7.6 ppm (d)

-continued

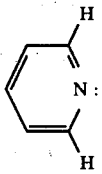  δ = 8.6 ppm (d)

EXAMPLE 15

1-(2-Methoxyphenyl) 3-(4-pyridyl) 2-propene-1-one

The procedure is as in Example 11, starting from 15 g of 2-methoxyacetophenone and 20.4 g of pyridine-4-carbaldehyde in 50 ml of methanol and using 45 ml of a 2.5 N aqueous sodium hydroxide solution in place of the 11 N solution. 7 g of 1-(2-methoxyphenyl) 3-(4-pyridyl) 2-propene-1-one which melts at 70° C. are obtained.

NMR spectrum of the product obtained (solvent CDCl$_3$):

  δ = 7.6 ppm (s)

OCH$_3$ :        δ = 3.95 ppm (s)
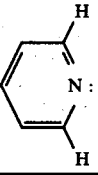  δ = 8.6 ppm (d)

EXAMPLE 16

4-[3-(phenyl)propyl]piperidine

A well stirred suspension containing 19.7 g of 4-[3-(phenyl)propyl]piperidine (prepared according to K. B. Prasad et al., J. Chem. Soc. Ser. C, 1969, 2134) in solution in 300 ml of acetic acid and 2 g of Adams platinum oxide is maintained, at ambient temperature, under a hydrogen pressure corresponding to an excess pressure of 50 mm of water relative to atmospheric pressure, until the absorption of gas has ceased.

The platinum is then separated by filtration, then the acetic solution is concerned. The residue is diluted by 300 ml of water, the pH is adjusted to 10 by the addition of potassium carbonate and the mixture is extracted twice with 300 ml of chloroform. The collected chloroform fractions are dried over magnesium sulfate, then concentrated. 19.2 g of an impure product are obtained which, after acidification with HCl and crystallization in acetone, furnishes 18.8 g of 4-[3-(phenyl)propyl]piperidine in the form of the hydrochloride melting at 167° C.

Analysis for C$_{14}$H$_{21}$N, CHl: Calc. % C 70; % H 9.2; % N 5.58. Found % C 70.15; % H 9.21; % N 5.69.

EXAMPLE 17

4-[3-(4-Aminophenyl)propyl]piperidine

By hydrogenating, according to the method of Example 16, 29.7 g of 4-[3-(4-nitrophenyl)propyl]pyridine, a mixture is obtained, the constituents of which are separated by chromatography on a silica column (eluant: mixture of 90 parts by volume of chloroform and 10 parts by volume of diethylamine). After acidification with HCl of the separated fractions, 1.8 g of the hydrochloride of 4-[3-(4-aminophenyl)propyl]piperidine which melts at 250° C. are obtained.

NMR spectrum of the product obtained (solvent CDCl$_3$):

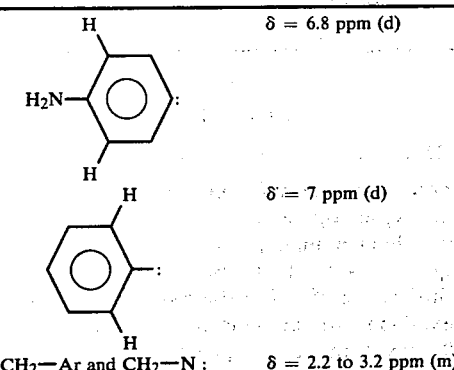

| | |
|---|---|
| H (on aminophenyl) | δ = 6.8 ppm (d) |
| H (on aminophenyl) | δ = 7 ppm (d) |
| CH$_2$—Ar and CH$_2$—N : | δ = 2.2 to 3.2 ppm (m) |

The starting product, 4-[3-(4-nitrophenyl)propyl]pyridine is prepared as follows:

Into a solution consisting of 10.3 ml of pure acetic acid and 18.6 ml of 98% sulfuric acid, cooled to 5° C., are introduced slowly, drop by drop, 25 g of 4-(3-phenylpropyl) pyridine. When this addition has been completed, the solution obtained is cooled to −15° C. and a sulfonitric mixture consisting of 9 ml of nitric acid and 18.6 ml of 98% sulfuric acid is added drop by drop. During the whole of the addition the temperature of the reaction medium is maintained below +10° C. The addition is completed in one hour. The yellow solution obtained is poured into 600 g of a water+ice mixture. The pH is adjusted to 11 by the addition of an aqueous potassium hydroxide solution and the mixture is extracted twice with 200 ml of ether. The ethereal phases are collected and washed with water, dried over magnesium sulfate and concentrated. 29.7 g of 4-[3-(4-nitrophenyl)propyl]pyridine are obtained.

NMR spectrum of the product obtained (solvent CDCl$_3$):

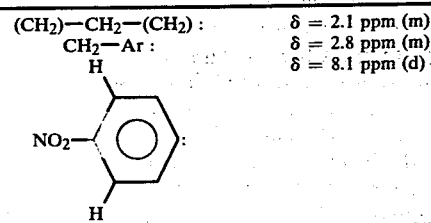

| | |
|---|---|
| (CH$_2$)—CH$_2$—(CH$_2$) : | δ = 2.1 ppm (m) |
| CH$_2$—Ar : | δ = 2.8 ppm (m) |
| H | δ = 8.1 ppm (d) |

EXAMPLE 18

1-(2-Acetylaminophenyl) 3-(4-piperidyl) 1-propanone

A well-stirred suspension consisting of 43.5 g of 1-(2-acetylaminophenyl) 3-(4-pyridyl) 2-propene-1-one, 4.3 g of Adams platinum oxide and 450 ml of acetic acid is maintained, at ambient temperature, under a hydrogen pressure corresponding to an excess pressure of 50 mm of water relative to atmospheric pressure, until 8 equivalents of hydrogen have been absorbed.

The platinum is then separated by filtration and the acetic solution is concentrated. The residue is diluted by 500 ml of water, adjusted to pH 10 by a concentrated solution of sodium hydroxide, then extracted 3 times with 200 ml of ethyl acetate. The collected organic phases are washed twice with 50 ml of water, dried over magnesium sulfate, and then concentrated.

In this manner 38.4 g of a brown, oily product are obtained which after acidification to pH 5 by a hydrochloric acid solution in ether is converted to the hydrochloride. The recrystallization of the crude hydrochloride in ethanol furnishes 26 g of 1-(2-acetylaminophenyl) 3-(4-piperidyl) 1-propanone in the form of the hydrochloride melting at 217° C.

NMR spectrum of the product obtained (solvent CDL$_3$):

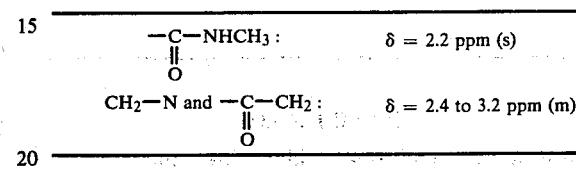

| | |
|---|---|
| —C(=O)—NHCH$_3$ : | δ = 2.2 ppm (s) |
| CH$_2$—N and —C(=O)—CH$_2$ : | δ = 2.4 to 3.2 ppm (m) |

The starting product, 1-(2-acetylaminophenyl) 3-(4-pyridyl) 2-propene-1-one is prepared as follows:

45 g of 1-(2-aminophenyl) 3-(4-pyridyl) 2-propene-1-one (product of Example 14) are contacted with 13.5 ml of acetic anhydride. After 10 minutes at 100° C., the solution obtained is cooled, diluted with 80 ml of water, then the pH is slowly adjusted to 6 (while maintaining the temperature at 5° C.) by the addition of a concentrated solution of sodium hydroxide. After stirring for one hour, the precipitate formed is filtered, washed with water, then dried at 80° C. under vacuum. 53 g of 1-(2-acetylaminophenyl) 3-(4-pyridyl) 2-propene-1-one which melts at 130° C. are obtained.

EXAMPLE 19

1-(4-Methoxylphenyl 3-(4-piperidyl) 1-propanone

A suspension of 49 g of 3-(1-benzoyl 4-piperidyl) 1-(4-methoxyphenyl) 1-propanone in 490 ml of a 5 N aqueous solution of hydrochloric acid is heated for 5 hours under reflux. After cooling, the pH is adjusted to 3–4 by the addition of a caustic soda lye, then the benzoic acid formed is extracted with 500 ml of ether.

The aqueous phase separated is made alkaline by the addition of a sodium hydroxide solution, then extracted with 250 ml of ethyl acetate. The organic phase is dried over magnesium sulfate, then concentrated. 39 g of crude product are obtained which, diluted in 240 ml of ethanol and acidified with 10 ml of a 7 N hydrochloric acid solution in ether, furnish 12 g of 1-(4-methoxyphenyl) 3-(4-piperidyl) 1-propanone in the form of the hydrochloride melting at 168° C.

Analysis for C$_{15}$H$_{21}$NO$_2$, HCl: Calc. % C 63.4; % H 7.76; % N 4.94. Found % C 63.81; % H 7.90; % N 4.71.

EXAMPLE 20

2-[3-(4-Piperidyl)propyl]phenol

A well-stirred solution containing 23 g of 1-(2-hydroxyphenyl) 3-(4-pyridyl) 3-hydroxy 1-propanone (prepared according to Corvaisier Bull. Soc. Chim. Fr. 1962, 528) in solution in 340 ml of pure acetic acid and 5 g of palladium charcoal with 10% of palladium is maintained at 80° C. under a hydrogen pressure corresponding to an excess pressure of 50 ml of water relative to atmospheric pressure, until the absorption of gas has ceased.

Afer cooling, the palladium charcoal is separated by filtration, then the acetic solution is concentrated. 11.5 g of a colorless oil are obtained, which, after recrystallization in an isopropanol-ethylacetate mixture, furnishes 5.3 g of 2-[3-(4-piperidyl)propyl]phenol which melts at 152° C.

Analysis for $C_{14}H_{21}NO$: Calc. % C 76.71; % H 9.59; % N 6.39. Found % C 76.49; % H 9.51; % N 6.42.

EXAMPLE 21

1-(4-Fluorophenyl) 3-(4-piperidyl) 1-propanone

The procedure is as in Example 19, starting from 12 g of 3-(1-benzoyl 4-piperidyl) 1-(4-fluorophenyl) 1-propanone. After acidification of the crude product obtained by means of a solution of hydrochloric acid in ether, 6.5 g of the hydrochloride of 1-(4-fluorophenyl) 3-(4-piperidyl) 1-propanone which melts at 188° C. are obtained.

NMR spectrum of the product obtained (solvent $CDCl_3$):

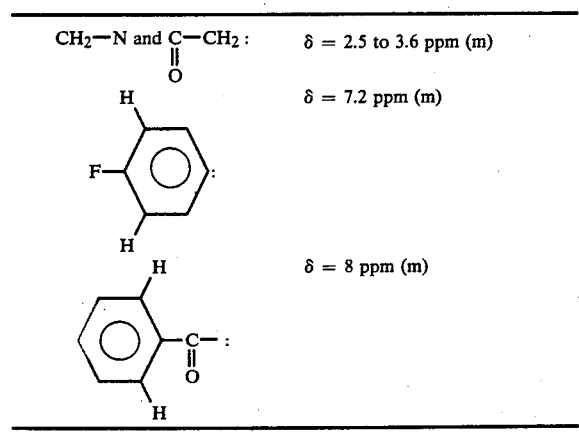

EXAMPLE 22

1-(4-Methoxyphenyl) 3-(4-piperidyl) 2-propanol

To a suspension of 10.2 g of 1-(4-methoxyphenyl) 3-(4-piperidyl) 1-propanone in 130 ml of dry tetrahydrofurane, maintained at 5° C. and under a nitrogen atmosphere, 2.8 g of lithium aluminum hydride are added in small portions. When the addition is complete, the reaction mixture is heated to 60° C. over five hours, then cooled to 0° C. Then, while maintaining this temperature, 25.2 ml of water are added very slowly. The mineral products are filtered and washed twice with 50 ml of hot methylenechloride. The collected organic solutions are concentrated by evaporation of the solvent. The oil obtained is dissolved in 150 ml of isopropanol and treated with 7.4 g of fumaric acid. In this manner, 7.8 g of 1-(4-methoxyphenyl) 3-(4-piperidyl) 1-propanol in the form of its fumarate are obtained.

Analysis for 3 ($C_{15}H_{23}NO_2$), 2 ($C_4H_4O_4$): Calc. % C 65; % H 7.86; % N 4.29. Found % C 64.8; % H 7.92; % N 4.19.

PHARMACOLOGICAL PROPERTIES (1) Antidepressive activity

It is known that the antidepressant products known at present have the property of inhibiting the uptake, by the neurons, of cerebral monoamines. They act simultaneously on the serotonin or 5-hydroxytryptamine (5HT) and on the catecholamines, notably on noradrenaline (NA), and have diverse secondary effects, in particular a cardiotoxicity.

A means for obtaining antidepressants which have less secondary effects than the drugs used at present consists in the search for products acting specifically on serotonin (J. Buuslassen et al., Europ. J. Pharmacol. 32, 108 (1975)).

The activity of the products of formula (I) has been demonstrated by means of the inhibition test of the uptake of cerebral monoamines by the synaptosomes of the rat brain, according to the method of Kannengeisser et al. (Biochem. Pharmacol. 22, 73, 1973). The results are expressed by a 50% inhibitory dose ($I_{50}$) which represents the dose of product, in micromoles per liter, diminishing by 50% the uptake of the neuromediator considered in the specific regions (hypothalamus, medulla+pons) where the corresponding neurons predominate.

TABLE I

| | $I_{50}$ ($\mu$M/L) | |
|---|---|---|
| Products | NA (hypothalamus) | 5HT (medulla + pons) |
| Example 6 | 2.2 | 0.02 |
| Example 7 | 3 | 0.01 |
| Example 8 | 0.9 | 0.09 |
| Example 9 | 1.3 | 0.18 |
| Example 10 | 0.3 | 0.16 |
| Example 16 | 0.24 | 0.002 |
| Imipramine | 0.5 | 0.12 |

Table I shows that the compounds of formula (I) are powerful inhibitors of the uptake of serotonin. They are frequently more active and above all much more selective than imipramine (reference product). They specifically inhibit the uptake of serotonin.

(2) Anxiolytic activity

The anxiolytic activity of the benzodiazepines is well known. The presence of specific receptors for benzodiazepines in the brain membranes of the rat has also been well established (Squires et al. Nature 266, 732, (1977)) and a good correlation exists between the degree of affinity of benzodiazepines for the receiving binding sites and the pharmacodynamic effects observed in the animal and in man.

This affinity is measured by the capacity of products for displacing the tritiated diazepam ($^3$H-diazepam) from its binding site and is expressed by a $K_i$ value in micromoles which is calculated by the formula:

$$K_i = I_{50}[(1+C)K_D]$$

wherein C represents the concentration of $^3$H-diazepam, $K_D$ is a constant of affinity equal to 2.74 $\mu$M and $I_{50}$ is the concentration necessary for obtaining an inhibition of 50% of the binding of the $^3$H-diazepam.

Up to now the affinity of the benzodiazepines for their cerebral receptors has shown to be an exclusive characteristic of that chemical series. In fact, no other drug, acting in other respects on the central nervous system has been found capable of displacing in a significant manner the diazepam from its binding sites (Braestrup et al, Eur. J. Pharmacol. 48, 263 (1978)).

The products of formula (I), although structurally different from the benzodiazepines, displace $^3$H-diazepam from its binding sites, as indicated by the results listed in the following Table II:

TABLE II

| Products | Ki (μM) |
|---|---|
| Example 6 | 19.5 |
| Example 7 | 45 |
| Example 8 | 36 |
| Example 10 | 42 |
| Example 17 | 36 |
| Example 20 | 29 |
| Example 19 | 6.5 |
| Example 22 | 32 |
| Imipramine | inactive |

The results of Table II have been obtained by testing the products according to the method of H. Mohler et al., Life Sciences 20, 2101 (1977).

The products of formula (I) thus are not only antidepressants but also anxiolytic drugs. The mechanism of action of these compounds (specific action on the uptake of serotonin and affinity for the cerebral receptors of the benzodiazepines) confers on them a wholly original psychotropic profile.

(3) Antiarhythmic activity

The antiarhythmic activity of the compounds of formula (I) has been demonstrated with the help of the aconitine test in rats.

The principle of the technique rests on the induction time of ventricular arhythmias caused by aconitine which is slowly perfused in rats. An antiarhythmic substance retards the occurrence of arhythmias and this delay is proportional to the activity of the molecule.

Groups of five male rats are used. An individual anaesthesia is realized (10% urethane: 1 g/kg/ip) to allow a catheterization of the vein of the penis. The electrocardiogram is recorded. At time T=0 the substance investigated is injected in the form of an aqueous solution, at a rate of 2.5 ml of solution per kg in 30 seconds. At time T=90 seconds, that is 1 minute after the end of the injection, aconitine is perfused at a rate of 20 μg per minute until the appearance of supra-ventricular systoles. The time of perfusion of the aconitine is noted.

The results are expressed by an $ED_{50}$, which is the dose in mg/kg increasing by 50% the perfusion time of aconitine in comparison with the perfusion time of aconitine for the control animals.

The products of formula (I) present remarkable antiarhythmic properties, as is shown by way of example by the results listed in the following Table III:

TABLE III

| Products | $ED_{50}$ (i.v.) mg/kg |
|---|---|
| Example 16 | 2.5 |
| Example 20 | 1.2 |
| Quinidine (reference product) | 4 |

TOXICOLOGICAL PROPERTIES

The acute toxicities of the compounds of formula (I) have been determined on the male mouse $CD_1$ (Charles River) per os. The $LD_{50}$ have been calculated, after 3 days of observation, by the cumulative method of J. J. Reed and H. Muench (Amer. J. Hyg. 27, 493, (1938)).

The products of formula (I) behave as substances of low toxicity to the mouse, as shown by the $LD_{50}$ listed, by way of example in the following Table IV:

TABLE IV

| Products | Acute toxicity in the mouse (per os) $LD_{50}$ (in mg/kg) |
|---|---|
| Example 6 | 400 |
| Example 7 | 225 |
| Example 8 | 235 |
| Example 9 | 600 |
| Example 10 | 400 |
| Example 16 | 200 |
| Example 19 | 200 |
| Example 22 | 800 |

THERAPEUTIC UTILIZATION

The compounds of formula (I) and their salts with pharmaceutically acceptable acids may be used in human therapy in the form of tablets, capsules, pills, suppositories, ingestible or injectable solutions, etc. for the treatment of diverse psychic disorders with depressive and anxiety component and for the treatment of arhythmias.

The posology depends upon the effects sought and on the manner of administration used. If given orally, for example, it may be comprised between 5 and 250 mg of active substance per day, with unit doses from 1 to 50 mg.

The pharmaceutically acceptable acids, include, for example, organic acids such as acetic, propionic, tartaric, citric and methanesulfonic acids, and inorganic acids such as hydrochloric, hydrobromic and sulfuric acids.

What is claimed is:

1. A pharmaceutical composition, particularly useful as an antiarhythmic and for the treatment of states of depression and anxiety, which contains as an active agent a pharmaceutically effective amount of a compound corresponding to the formula:

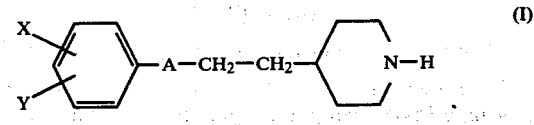

wherein X and Y are the same or different and represent hydrogen, halogen, alkyl containing 1 to 4 carbon atoms, alkoxy containing 1 to 4 carbon atoms, alkylthio containing 1 to 4 carbon atoms, trifluoromethyl, hydroxy, amino, monoalkylamino containing 1 to 4 carbon atoms or amino substituted by alkylsulfonyl containing 1 to 4 carbon atoms, by alkylcarbonyl containing 1 to 5 carbon atoms or by benzoyl, and A represents

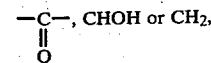

or a salt of said compound with a pharmaceutically acceptable acid, in a pharmaceutically acceptable carrier.

2. A pharmaceutical composition in accordance with claim 1 wherein the active agent is 4-[3-(phenyl)-propyl]piperidine or a salt thereof with a pharmaceutically acceptable acid.

3. A chemical compound corresponding to formula (I) of claim 1 wherein A is CHOH and X and Y have the same definitions as in claim 1.

4. A chemical compound corresponding to formula (I) of claim 1, wherein A is CH₂, Y is hydrogen or halogen or alkyl containing 1 to 4 carbon atoms, alkoxy containing 1 to 4 carbon atoms, alkylthio containing 1 to 4 carbon atoms, trifluoromethyl, hydroxy, amino, monoalkylamino containing 1 to 4 carbon atoms, or amino substituted by alkylsulfonyl containing 1 to 4 carbon atoms, by alkylcarbonyl containing 1 to 5 carbon atoms or by benzoyl and X is halogen or alkylthio containing 1 to 4 carbon atoms, alkoxy containing 2 to 4 carbon atoms, trifluoromethyl, hydroxy, amino or monoalkylamino containing 1 to 4 carbon atoms or amino substituted by alkylsulfonyl containing 1 to 4 carbon atoms, by alkylcarbonyl containing 1 to 5 carbon atoms or by benzoyl.

5. A method for the treatment of a human afflicted with arhythmia, anxiety or depression which comprises administering to said human an effective amount of a compound corresponding to formula (I) of claim 1 or a salt of said compound with a pharmaceutically acceptable acid.

6. A chemical compound of the formula:

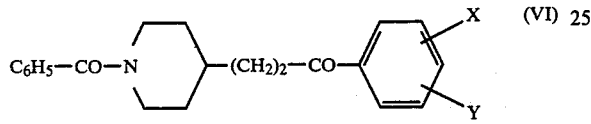

(VI)

wherein the substituent X is fixed in the 4-position and is halogen or alkyl or alkoxy containing 1 to 4 carbon atoms and the substituent Y is fixed in the 3-position and is hydrogen or halogen.

7. A chemical compound of the formula:

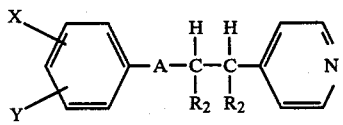

(II)

wherein A is

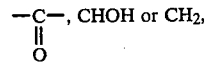

$R_1$ is hydrogen, $R_2$ is hydrogen or OH, or $R_1$ and $R_2$ together form a single bond, X is fluorine, alkoxy containing 2 to 4 carbon atoms, alkylthio containing 1 to 4 carbon atoms, trifluoromethyl, amino, monoalkylamino containing 1 to 4 carbon atoms or amino substituted by alkylsulfonyl containing 1 to 4 carbon atoms, by alkylcarbonyl containing 1 to 5 carbon atoms or by benzoyl, and Y is hydrogen or halogen or alkyl containing 1 to 4 carbon atoms, alkoxy containing 1 to 4 carbon atoms, alkylthio containing 1 to 4 carbon atoms, trifluoromethyl, hydroxy, amino, monoalkylamino containing 1 to 4 carbon atoms, or amino substituted by alkylsulfonyl containing 1 to 4 carbon atoms, by alkylcarbonyl containing 1 to 5 carbon atoms or by benzoyl.

8. A chemical compound of the formula:

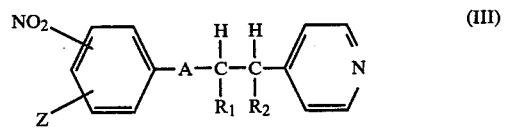

(III)

wherein A is

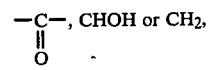

$R_1$ is hydrogen, $R_2$ is hydrogen or OH, or $R_1$ and $R_2$ together form a single bond, and Z is hydrogen or halogen or alkyl containing 1 to 4 carbon atoms, alkoxy containing 1 to 4 carbon atoms, alkylthio containing 1 to 4 carbon atoms, trifluoromethyl, hydroxy, amino, monoalkylamino containing 1 to 4 carbon atoms, or amino substituted by alkylsulfonyl containing 1 to 4 carbon atoms, by alkylcarbonyl containing 1 to 5 carbon atoms or by benzoyl.

* * * * *